(12) United States Patent
Carter et al.

(10) Patent No.: US 7,314,461 B2
(45) Date of Patent: Jan. 1, 2008

(54) PRECALIBRATED INFLATION DEVICE FOR BALLOON CATHETER

(75) Inventors: Matthew P. Carter, Dobson, NC (US); Gregory J. Skerven, Kernersville, NC (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 199 days.

(21) Appl. No.: 10/422,553

(22) Filed: Apr. 23, 2003

(65) Prior Publication Data

US 2004/0019323 A1 Jan. 29, 2004

Related U.S. Application Data

(60) Provisional application No. 60/375,245, filed on Apr. 23, 2002.

(51) Int. Cl.
*A61M 29/00* (2006.01)
(52) U.S. Cl. .............. 604/96.01; 604/97.01; 604/97.03; 604/99.01
(58) Field of Classification Search .......... 604/96.01, 604/97.01, 97.03, 98.01, 99.02, 100.01, 100.03
See application file for complete search history.

(56) References Cited

U.S. PATENT DOCUMENTS

| | | | | |
|---|---|---|---|---|
| 4,384,470 A | * | 5/1983 | Fiore | ............... 73/1.68 |
| 4,446,867 A | * | 5/1984 | Leveen et al. | ............... 606/194 |
| 4,693,706 A | * | 9/1987 | Ennis, III | ............... 604/87 |
| 4,714,460 A | * | 12/1987 | Calderon | ............... 604/28 |
| 4,762,127 A | * | 8/1988 | Narayanan et al. | ............... 606/156 |
| 5,868,713 A | * | 2/1999 | Klippenstein | ............... 604/195 |
| 6,110,200 A | | 8/2000 | Hinnenkamp | |
| 6,120,481 A | | 9/2000 | Rennert et al. | |
| 6,234,996 B1 | * | 5/2001 | Bagaoisan et al. | ....... 604/97.01 |
| 6,319,229 B1 | | 11/2001 | Kim et al. | |
| 6,322,526 B1 | | 11/2001 | Rosenman et al. | |

* cited by examiner

*Primary Examiner*—Kevin C. Sirmons
*Assistant Examiner*—Phillip Gray
(74) *Attorney, Agent, or Firm*—Brinks Hofer Gilson & Lione

(57) ABSTRACT

A medical device including an inflation element, such as a syringe, and a balloon catheter in which the inflation element includes a series of indicia to which an operative portion of the inflation device can be aligned. The indicia directly correspond to a particular balloon diameter. A method of inflating a balloon to at least two desired diameters in a body lumen and determining the inflation diameter of the balloon within the body lumen. A method of calibrating the inflation device to allow a user to inflate a balloon to a desired diameter.

24 Claims, 2 Drawing Sheets

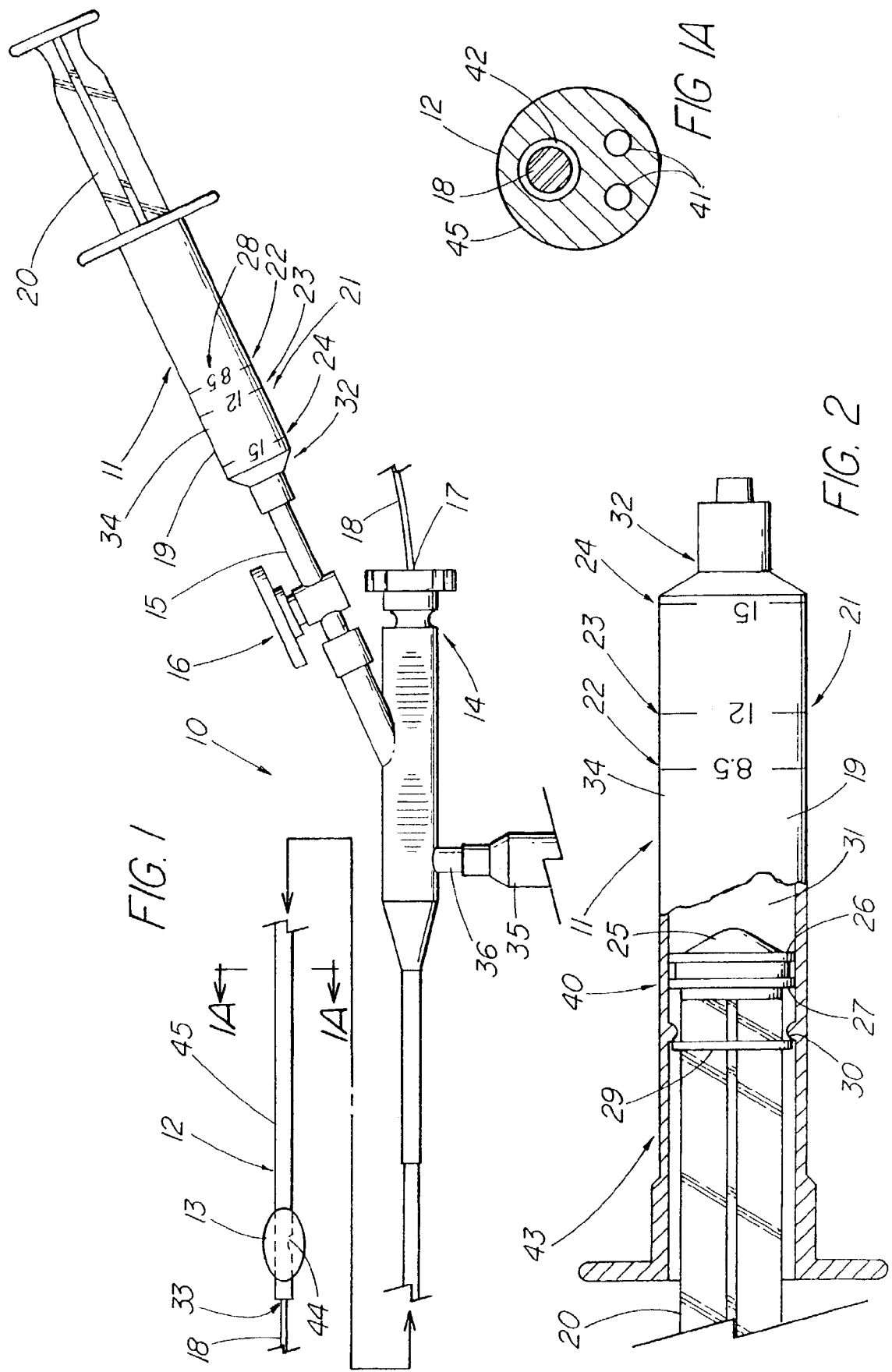

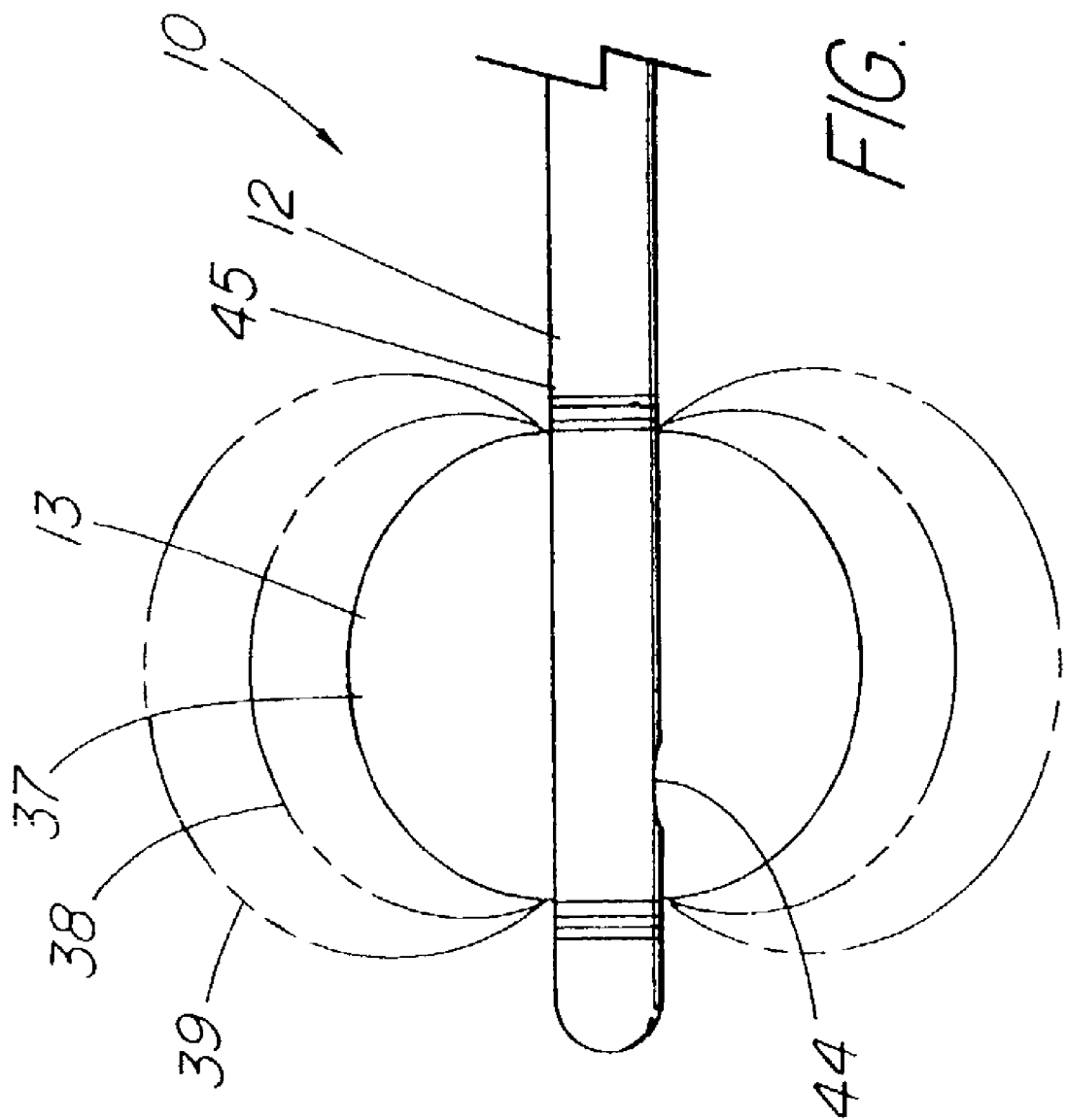

PRECALIBRATED INFLATION DEVICE FOR BALLOON CATHETER

RELATED APPLICATIONS

This claims the benefit of U.S. Provisional Application Ser. No. 60/375,245, filed Apr. 23, 2002, entitled "Precalibrated Inflation Device For Balloon Catheter."

TECHNICAL FIELD

This invention relates to medical devices, more particularly to inflation devices used in combination with a balloon catheter.

BACKGROUND OF THE INVENTION

Balloon catheters are commonly used in endoscopic procedures in the biliary tree, such as to extract stones and calculi obstructing the bile duct or pancreatic duct. In such a procedure, the endoscopist typically performs a sphincterotomy at the opening to the common bile duct then replaces the sphincterotome with a balloon catheter and advances it over the indwelling wire guide past the stone. Contrast media is usually injected prior to introduction of the balloon catheter so that the obstruction can be located fluoroscopically and also, to help determine what size of extraction balloon would be most appropriate. The balloon, which is made of latex or some other compliant material, is then fully inflated in the duct to assess the optimum balloon diameter for sweeping the stone from the duct. Generally there is a predetermined amount of infuscate delivered to achieve the nominal volume and diameter of the balloon. Often the endoscopist will elect to deflate the balloon slightly in order to perform the procedure, especially if the nominal or fully inflated diameter of the balloon is too large for the duct. Another reason is that a fully inflated balloon is more taut and thus, more subject to rupture when contacting a sharp edge of a stone within the duct. A partially deflated balloon is more forgiving and less likely to puncture. One problem with partially deflating the balloon to sweep the stone is that the operator cannot readily determine the diameter of the balloon following deflation and thus, must make an educated guess as to whether it is appropriate for that particular patient's anatomy. The problem is that the calibrations on an inflation device typically refer only to the actual volume being delivered and thus, require that the operator be able to calculate the syringe volume that corresponds to a given balloon size. If a mark is provided that corresponds to the nominal size of that particular balloon, it is of limited use if trying to extrapolate to inflate or deflate to another size. Since the balloon diameter cannot be easily adjusted downward to a known value using a conventional inflation device, a smaller balloon must be used and inflated to the nominal size to achieve certainty of size. This means that the fully inflated smaller balloon may be less forgiving in case of contact with a sharp edge. Because compliant balloons can assume a range of diameters to address a specific need, what is needed is a system that allows the operator to be able to use a single balloon and be able to determine and control the diameter as needed.

SUMMARY OF THE INVENTION

The foregoing problems are solved and a technical advance is achieved in an illustrative inflation device and a balloon catheter apparatus in which the inflation device includes a series of indicia to which an operative portion of the inflation device (e.g., a plunger head) can be aligned. Each indicia marking corresponds to a particular volume of air or liquid that produces a balloon diameter indicated at the mark when the inflation device is deployed. In an exemplary embodiment, the balloon catheter comprises a biliary stone extraction balloon in which the balloon portion comprises latex or another compliant elastomeric material. In a first embodiment used for the extraction of stones within the biliary or pancreatic ducts, the inflation device comprises a standard 5 ml plastic syringe with a luer fitting that is connectable to a port communicating with the inflation lumen of the balloon catheter. The inflation device includes a stop to hold the plunger at a first position and three indicator markings that correspond to the position to where the plunger head of the syringe should be advanced to result in the balloon being filled to a diameter of 8.5, 12, and 15 mm, respectively. The numerical value of the resultant balloon diameter is indicated next to the mark. In the exemplary embodiment, the leading edge of the first seal of the plunger head is advanced to the mark to achieve the corresponding balloon size. This allows the operator to readily adjust the balloon diameter by inflating or deflating the balloon accordingly without having to calculate or calibrate the volume of air necessary to produce the desired results.

BRIEF DESCRIPTION OF THE DRAWING

Embodiments of the present invention will now be described by way of example with reference to the accompanying drawings, in which:

FIG. 1A depicts a size view of the illustrative embodiment of the present invention;

FIG. 1 a depicts a cross-sectional view taken along Line 1A-1A of FIG. 1;

FIG. 2 depicts a partially sectioned side view of the inflation device of the embodiment of FIG. 1; and FIG. 3 depicts an enlarged side view of the balloon portion of the embodiment of FIG. 1.

DETAILED DESCRIPTION

FIGS. 1-3 depict the illustrative balloon apparatus 10 of the present invention which comprises a balloon catheter 12 that includes a shaft portion 44 and balloon portion 13 affixed thereto just proximal to the distal tip 33 of the shaft. The balloon portion 13 is made of a compliant material such as latex, silicone, or another suitable elastomeric material that can allow the balloon to assume a range of diameters, unlike a non-compliant balloon which is inflatable to a single, maximum diameter. The present balloon apparatus 10 further comprises an inflation device 11, such as the illustrative syringe, which includes a plurality of unique indicia 21 that indicate the predetermined position where the operative portion 20 (e.g., the illustrative plunger) of the inflation device 11 must be advanced or withdrawn to deliver the proper amount of fluid 31, such as air, to achieve the desired balloon diameter 37, 38, 39, respectively (see FIG. 3). The corresponding diameter is indicated in some manner at that particular mark 22, 23, 24 located on the surface 34 of the syringe barrel 19, typically by the appropriate corresponding numerical value 28. Because the internal volume of each model of balloon catheter can vary, the syringe 11 must be pre-calibrated for that particular balloon catheter 12 design so that the indicia 21 accurately indicate the positions to which the inflation device 11 should be advanced. Alternatively, the inflation device 11 may comprise any appropriate manually operated or electromechanical device that is intended for delivering a measurable amount of gas or liquid for inflating a balloon in a medical application. For example, it is contemplated that the series of unique indicia 21 comprise separate buttons or switches that activate the operative portion 20 of the inflation device 11 to deliver a different pre-measured amount of infuscate 31 to the balloon 13.

As depicted in FIGS. 1 and 1A, the illustrative balloon apparatus 10, which is used for sweeping gall stones, calculi, or other obstructions from the biliary tree, comprises a triple-lumen balloon catheter 12, such as a Howell DASH™ Extraction Balloon (Wilson-Cook Medical, Inc.), having a first pair of small lumens 41 dedicated for inflation of the balloon, and a third, larger lumen 42 for both accommodating a standard wire guide 18 and providing a pathway for infusion of contrast media or other agents around the wire guide 18. Each lumen extends through the shaft portion of the catheter proximally from the distal end 33 or balloon portion 13, where they communicate with a port 15, 17, 36 located on the proximal hub assembly 14 of the device. The first pair of lumens 41 provide communication between the a balloon inflation port 44, (a scive in the catheter tubing located within the balloon 13) and the proximal inflation port 15, which is a luer fitting located at the proximal end of an optional stopcock 16 used to help prevent loss of air pressure once the balloon has been inflated. The distal end 32 of the inflation syringe 11 is configured to couple with the luer fitting (inflation port 15). The third lumen 42, which is generally larger because of its dual function, communicates with both the infusion port 36, which is configured to receive a second syringe 35 for injection of contrast media or other agents (such as saline for flushing) and a wire guide port 17, such as a Tuohy-Borst fitting. The two ports 17, 36 merge to form a common pathway that comprises the second lumen 42. The inflation device 11 of the present invention includes a plurality of unique indicia 21 comprising a first, second and third indicium or marking 22, 23, 24 disposed along the length thereof which includes the corresponding numerical value 28 alongside. The indicia are printed in ink on the outer surface 34 of the syringe barrel, although they can be etched, embossed, or otherwise applied thereto or incorporated thereinto. Alternatively, other types of unique indicia (i.e., other alphanumeric characters, symbols, colors, etc.) may be utilized to correspond with any calibrated balloon diameters 37, 38, 39 that one wants to identify.

Referring now to FIGS. 2 and 3, the illustrative inflation syringe 11 includes a stop 30 which comprises a pair of protuberances on the inside of the syringe barrel 19 that temporarily lock the plunger 20 at the designated pre-deployment 43 position. The rear edge 29 or flange of the plunger head 25 is configured to rest against the stop 30 until additional force is applied during deployment to overcome resistance provided by the stop 30. The plunger 20 is then advanced to the marking 21 corresponding to the desired balloon size. The first marking 22 corresponds to the position to which the plunger 20 of the inflation syringe 11 is advanced to achieve a first balloon diameter 37 of 8.5 mm. To inflate the balloon to the first diameter, the plunger head 25, which includes a distal and a proximal seal 26, 27, is positioned such that the leading edge of the distal seal 26 is aligned at the mark 22. Typically, the plunger head must be advanced beyond the first mark 22 (e.g., to the second mark 23) and subsequently withdrawn back to the first mark 22 when inflating the balloon 13 to the smaller diameters, such as 8.5 mm. This is generally not necessary for the larger balloon diameters. The plunger head is aligned with the second mark 23 to inflate (or deflate) the balloon to the second diameter 38 (12 mm) or aligned with the third mark 24 (essentially the full deployment of the syringe contents 31) to inflate the balloon 13 to the third diameter 39, which is about 15 mm. While these diameters represent the most commonly available biliary extraction balloon sizes, any precalibrated balloon diameters may be indicated depending on the application or the physician preference. In addition, the present invention may be adapted for vascular, pulmonary, genitourinary, or other gastrointestinal uses which might require a different range and set of balloon diameters.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. Unless otherwise indicated, all ordinary words and terms used herein shall take their customary meaning as defined in *The New Shorter Oxford English Dictionary,* 1993 *edition*. All technical terms shall take on their customary meaning as established by the appropriate technical discipline utilized by those normally skilled in that particular art area. All medical terms shall take their meaning as defined by *Stedman's Medical Dictionary,* 27*th edition.*

What is claimed is:

1. A medical system, comprising:
    a balloon inflatable to two or more inflated diameters, each diameter measurable in a unit of length; and
    an inflation element operably connected to the balloon and adapted for changing the inflated diameter of the balloon, the inflation element comprising;
        a barrel having two or more markings, each marking expressing the unit of length equal to each inflated diameter of the balloon; and
        a plunger movable relative to the barrel for inflating, deflating and re-inflating the balloon;
    wherein the two or more diameters are directly ascertainable by reference to a position of the plunger relative to the two or more markings whether the balloon is inflated, deflated or re-inflated without recalculation between inflation, deflation or re-inflation to the two or more inflated diameters.

2. The medical system of claim 1, further comprising a protuberance adapted to restrict proximal movement of the plunger beyond a predetermined position relative to the barrel.

3. The medical system of claim 1, further comprising a third unit of length marking on the barrel equal to a third inflation diameter of the balloon.

4. The medical system of claim 3 wherein each adjacent pair of markings comprise a different spacing therebetween.

5. The medical system of claim 3, wherein the first, second and third inflated diameters are 8.5, 12 and 15 mm, respectively.

6. The medical system of claim 1, further comprising a distal tip on the barrel wherein the distal tip is attachable to a luer fitting.

7. The medical system of claim 6, further comprising a stopcock operably connected to the luer fitting.

8. The medical system of claim 1, further comprising a catheter having a first passageway extending at least partially therethough, the passageway having a distal portion operably connected to the inflation element and a proximal portion operably connected to the balloon.

9. The medical system of claim 8, wherein the catheter further comprises a second passageway adapted to receive a wire guide.

10. The medical system of claim 8, wherein the catheter further comprises a dual function passageway having a distal portion and a proximal portion and extending at least partially parallel to the first passageway, the dual function passageway adapted to receive a wire guide and a fluid.

11. A medical system, comprising:
a balloon having at least a first inflated diameter of x mm and a second inflated diameter of y mm, the second diameter being greater than the first diameter; and
an inflation device adapted for inflating, deflating and re-inflating the balloon between the first and second diameters, the inflation device comprising:
an outer sleeve comprising at least a first balloon diameter marking of x mm, and a second balloon diameter marking of y mm, the first and second markings corresponding to the first and second inflated diameters of the balloon;
a plunger movable in relation to the outer sleeve and adapted for adjusting the balloon between the first inflated diameter and the second inflated diameter to increase or decrease the balloon to the second diameter or the first diameter, respectively; and
a protuberance adapted to restrict proximal movement of the plunger beyond a predetermined position relative to the outer sleeve to maintain an inflation volume within the inflation device and the balloon such that the first and second inflated diameters correspond to the first and second markings when the balloon is inflated or deflated without recalculation between inflation or deflation.

12. The medical system of claim 11, further comprising a catheter having a shaft extending between a distal portion and a proximal portion and a first passageway extending at least partially along the longitudinal shaft, wherein the distal portion is operably connected to the inflation device and the proximal portion is operably connected to the balloon.

13. The medical system of claim 12, wherein the catheter further comprises a second passageway extending at least partially along the shaft.

14. The medical system of claim 12, wherein the second passageway comprises an infusion port for delivery of a fluid.

15. The medical system of claim 14, wherein the fluid comprises contrast media.

16. The medical system of claim 11, wherein the balloon comprises an elastomeric material.

17. The medical system of claim 16 wherein the elastomeric material is latex or silicone.

18. A method for inflating a balloon to a pre-determined diameter within a body lumen, the method comprising:
providing a medical system comprising:
a balloon inflatable to at least a first and a second inflated diameter, the second diameter being greater than the first diameter; and
an inflation element adapted to inflate the balloon, the inflation element comprising an outer sleeve and a plunger, the outer sleeve having at least a first and a second balloon diameter marking, the first marking expressing a first unit of length equal to the first inflated diameter and the second marking expressing a second unit of length egual to the second inflated diameter;
retracting the plunger to fill the inflation element with an inflation volume;
inserting the balloon into a body lumen; and
depressing the plunger to align the plunger with the second marking to inflate the balloon to the second inflated diameter;
deflating the balloon to the first inflated diameter without recalculation by retracting the plunger toward a proximal end of the inflation element to align the plunger with the first marking.

19. The method of claim 18, further comprising depressing the plunger to align the plunger with the second marking to re-inflate the balloon to the second diameter.

20. The method of claim 18, further comprising providing a catheter for inserting the balloon to the body lumen.

21. The method of claim 18, wherein the balloon is inflatable to a third diameter, the third diameter indicating a third unit of length equal to a third balloon diameter marking on the outer sleeve.

22. A medical system, comprising:
a first syringe adapted to inflate a balloon, the first syringe comprising:
a barrel having two or more balloon diameter markings, each of the two or more markings expressing a unit of length equal to an inflated diameter of the balloon;
a plunger movable relative to the two markings, wherein the inflated diameter is directly ascertainable by reference to the position of the plunger relative to the two balloon diameter markings without recalculation; and
a protuberance adapted to restrict proximal movement of the plunger beyond a predetermined position relative to the barrel, the protuberance thereby preventing over-inflation of the balloon;
a catheter adapted to connect the first syringe to the balloon, the catheter comprising:
a longitudinal shaft having a first passageway extending between a distal portion operably connected to the balloon and a proximal portion operably connected to the inflation element; and
a dual function passageway extending along the longitudinal shaft, the dual function passageway being adapted to receive a second syringe and a wireguide.

23. The medical system of claim 1, wherein the unit of length is measured in mm.

24. The medical system of claim 1, wherein the barrel does not include volumetric markings.

* * * * *